United States Patent [19]

Kawagishi et al.

[11] 4,404,271
[45] Sep. 13, 1983

[54] METAL COMPLEXES FOR USE IN DEVELOPERS FOR ELECTROSTATIC IMAGES, CHARGE CONTROL FUNCTION

[75] Inventors: Yoji Kawagishi, Yawata; Yukihiko Ishida, Neyagawa; Kazuhiro Ishikawa, Nara, all of Japan

[73] Assignee: Orient Chemical Industries, Ltd., Japan

[21] Appl. No.: 329,996

[22] Filed: Dec. 11, 1981

[30] Foreign Application Priority Data

Dec. 22, 1980 [JP] Japan .................. 55-182388

[51] Int. Cl.$^3$ ............................ G03G 9/00
[52] U.S. Cl. .................... 430/110; 430/115; 430/904
[58] Field of Search ................ 430/110, 115; 260/438 S, 439

[56] References Cited

U.S. PATENT DOCUMENTS

| | | | |
|---|---|---|---|
| 3,320,169 | 5/1967 | East et al. | 430/110 |
| 3,826,747 | 7/1974 | Nagashima | 430/110 X |
| 3,991,226 | 11/1976 | Kosel | 430/114 |
| 4,024,084 | 5/1977 | Sittardt | 260/438 S |
| 4,206,064 | 1/1980 | Kinchi | 430/115 |

*Primary Examiner*—John D. Welsh

*Attorney, Agent, or Firm*—McGlew and Tuttle

[57] ABSTRACT

A complex system for developing electrostatic images, and particularly a toner which contains a metal complex represented by the formula

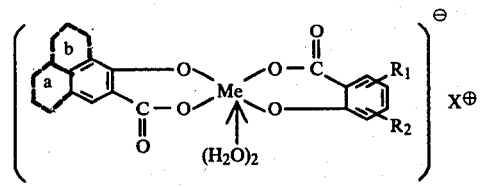

wherein a or b is a benzene ring moiety or cyclohexene ring moiety with or without $C_4$–$C_9$ alkyl substituents, $R_1$ and $R_2$ are each hydrogen, $C_4$–$C_9$ alkyl or a substituent which may be in the form of a benzene ring moiety or cyclohexene ring moiety with or without $C_4$–$C_9$ alkyl substituents, provided that both $R_1$ and $R_2$ are not hydrogen at the same time, Me is Cr, Co or Fe, and X is a counter ion such as hydrogen or sodium. The metal complex has good compatibility with the resin component of the toner and is substantially colorless, imparting outstanding durability to the toner.

31 Claims, No Drawings

METAL COMPLEXES FOR USE IN DEVELOPERS FOR ELECTROSTATIC IMAGES, CHARGE CONTROL FUNCTION

FIELD AND BACKGROUND OF THE INVENTION

The present invention relates to novel toner agents in general and, in particular, to metal-containing complexes usable in toners for developing electrostatic images in electrophotography, electrostatic recording, electrostatic printing, etc.

Conventional processes for converting latent electrostatic images to visible images are generally divided into two groups: liquid developing processes which use a developer comprising an electrically insulating liquid and a finely divided toner dispersed therein, and dry developing processes, such as the cascade process, fur brush process, magnetic brush process and powder-cloud process, in which a finely divider toner prepared by dispersing a coloring agent in a natural or synthetic resin is used singly or admixed with a solid carrier. The toners useful for such processes are charged positively or negatively in accordance with the polarity of the latent electrostatic image to be developed.

The toner can be made to retain electric charges by utilizing the triboelectric properties of the resin component of the toner, but since the toner is not highly chargeable by this method, the toner image obtained by development is prone to fogging and in turn to being obscure. To give the desired triboelectric properties to the toner, dyes and pigments for affording enhanced chargeability and further more charge control agents (triboelectrification control agents) are added to the toner. Presently used in the art for this purpose are oil-soluble nigrosine dyes for positively charging toners as disclosed in Published Examined Japanese Patent Application No. 2427/1966, and metal-containing complex dyes for negatively charging toners as disclosed in Published Examined Japanese Patent Application No. 26478/1970.

However, such dyes and pigments generally have low compatibility with the resin component of the toner, and are therefore difficult to disperse uniformly in the toner and tend to permit uneven charging, with the result that fog occurs in the developed toner image to obscure the image. Furthermore, even when the developer exhibits satisfactory developing characteristics in the initial stage of use, particles will collapse owing to uneven particle sizes or to the low compatability of the dye or pigment with the resin component, consequently forming fine particles consisting only of the dye or pigment. The toner will then scatter about markedly, staining the interior of the copying machine and contaminating the carrier so as to lower the ability of the developer to perform in the desired manner. Thus, the aforesaid use of such a dye or pigment involves many drawbacks.

Additionally, one of the substantial drawbacks of conventional dyes or pigments for imparting chargeability is that they are themselves color materials. This is in conflict with the basic requirement that chargeability imparting agents which are colorless or have a pale color that can be regarded as substantially colorless must be used for toners having a specific color. Published Unexamined Japanese Patent Application No. 127726/1978 (and correspondingly U.S. Pat. No. 4,206,064) discloses a metal complex of salicylic acid or alkylsalicylic acid as a material fulfilling the aforesaid basic requirement, but this material objectionably has low compatibility with the resin component of the toner.

SUMMARY OF THE INVENTION

In connection with intensive research which has been conducted on compounds usable in toners of the foregoing general type, but which have good compatibility with the corresponding resin component, which can be regarded as substantially colorless and which are capable of negatively charging such toners, it has been advantageously found in accordance with the present invention that a metal-containing complex compound which is composed of a highly aromatic compound moiety and a highly oleophilic compound moiety, having alkyl, and the like, oleophilic substituents incorporated therein, and which is represented by the formula (I)

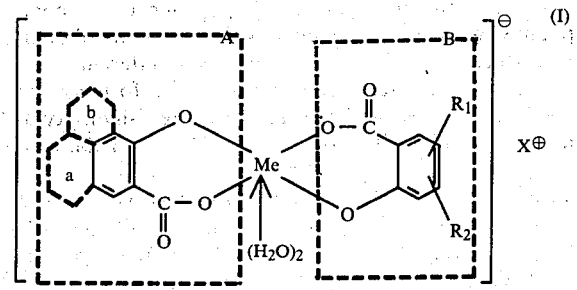

wherein a or b is a benzene ring or cyclohexene ring with or without $C_4$–$C_9$ alkyl substituents, $R_1$ and $R_2$ are each hydrogen, $C_4$–$C_9$ alkyl or a substituent which may be in the form of a benzene ring or cyclohexene ring with or without $C_4$–$C_9$ alkyl substituents, provided that both $R_1$ and $R_2$ are not hydrogen at the same time, Me is Cr, Co or Fe, and X is a counter ion, exhibits remarkably improved properties.

These properties specifically include remarkably improved compatibility and wettability with the corresponding resin components of the toner without impairing the charging properties of conventional coloring agents such as metal-containing complex dyes, and thus such metal-containing complex compound according to the present invention is useful as a charge control agent for providing toners having high durability and comprising chargeable particles of uniform quality.

Accordingly, it is among the objects and advantages of the present invention to provide metal-containing complex compounds usable in toners for developing electrostatic images in electrophotography, electrostatic recording, electrostatic printing, and the like, and especially toners containing such metal-containing compounds, in which the metal-containing complex compounds possess good compatibility with the corresponding resin components, constitute more or less substantially colorless constituents, are capable of negatively charging the corresponding toners, and more particularly possess good wettability with the corresponding resin component, all without impairing the charging properties of conventional metal-containing complex dyes usable in association therewith.

It is among the additional objects and advantages of the present invention to provide such metal-containing complex compounds as useful charge control agents for attaining toners having high durability and comprising chargeable particles of uniform quality.

Other and further objects of the present invention will become apparent from a study of the within specification and accompanying examples.

The various features of novelty which characterize the invention are pointed out with particularity in the claims annexed to and forming a part of this disclosure. For a better understanding of the invention, its operating advantages and specific objects obtained by its uses and inherent features, reference is made to the accompanying descriptive matter in which preferred embodiments of the invention are illustrated.

DESCRIPTION OF THE PREFERRED EMBODIMENTS

It will be appreciated that since the metal-containing complex compound of the present invention is a metal complex of such a compound A and such a compound B in the above formula(I), it will correspondingly be either a symmetrical metal complex when the compounds A and B are identical or an asymmetrical complex when the compounds A and B are different.

Examples of useful compounds A for forming the metal complexes of the formula (I) are 2-hydroxy-3-naphthoic acid; alkyl ($C_4$–$C_9$)-2-hydroxy-3-naphthoic acid; 5,6,7,8-tetrahydro-2-hydroxy-3-naphthoic acid; alkyl($C_4$–$C_9$)-5,6,7,8-tetrahydro-2-hydroxy-3-naphthoic acid; 1-hydroxy-2-naphthoic acid; alkyl($C_4$–$C_9$)-1-hydroxy-2-naphthoic acid; 5,6,7,8-tetrahydro-1-hydroxy-2-naphthoic acid; and the like, etc.

Corresponding examples of useful compounds B are alkyl($C_4$–$C_9$) salicylic acid; 3,5-dialkyl($C_4$–$C_9$)-salicylic acid; 2-hydroxy-3-naphthoic acid; alkyl($C_4$–$C_9$)-2-hydroxy-3-naphthoic acid; 5,6,7,8-tetrahydro-2-hydroxy-3-naphthoic acid; alkyl($C_4$–$C_9$)-5,6,7,8-tetrahydro-2-hydroxy-3-naphthoic acid; 1-hydroxy-2-naphthoic acid; alkyl($C_4$–$C_9$)-1-hydroxy-2-naphthoic acid; 5,6,7,8-tetrahydro-1-hydroxy-2-naphthoic acid; and the like, etc.

The metal complexes of the present invention can be prepared by a known process.

In the case of symmetrical metal complexes, the compound A is dispersed in a compatible vehicle such as in water or dissolved in a compatible solvent such as methanol, ethanol, ethyl cellosolve or the like. A metal imparting agent is admixed with the dispersion or solution in a mole ratio of substantially about 2:1. The mixture is then heated, and reacted with addition of a pH adjusting agent. The reaction mixture, when in the form of a slurry, is filtered to separate the desired product. When the reaction mixture is a solution, the mixture is diluted with water containing a mineral acid to form a precipitate, which is filtered off.

In the case of asymmetrical metal complexes, the compound B is dispersed in a compatible vehicle such as water or dissolved in a compatible solvent such as methanol, ethanol or the like, and a metal imparting agent is admixed with the dispersion or solution in a mole ratio of substantially about 1:1. The mixture is then heated, and reacted with addition of a pH adjusting agent to obtain a corresponding 1:1 type complex. Subsequently, a compound A is added to the product in a substantially equimolar ratio for reaction. The pH is about 3. The resulting precipitate is filtered off. The filter cake thus obtained has hydrogen ion as the counter ion when the pH is up to about 3.5. The filter cake is subjected to after-treatment in accordance with the purpose contemplated, as the artisan will appreciate.

The particular counter ion or cation can be changed according to the conditions of the after-treatment of the complex. For example when the precipitate is treated with a dilute mineral acid such as hydrochloric acid and thereafter washed until the pH of the liquid becomes about 6 to 7, the counter ion is the hydrogen ion. When the complex is treated with a base, such as an inorganic base, e.g. an aqueous solution of caustic soda, to a pH of about 10, the counter ion is the corresponding basic cation, e.g. the sodium ion.

Furthermore, to give the complex improved compatibility with a specific resin component, the complex can be converted to a complex of alkylamine.

Cr compounds, Co compounds and Fe compounds are usable as metal imparting agents according to the present invention. While complexes of such metal compounds are similar in charge controlling ability, according to the present invention, Fe complexes are slightly colored unlike the other complexes.

According to the present invention, a toner is prepared by admixing the instant metal-containing complex compound and a coloring agent with a known resin for toners.

Examples of useful resins in this regard are polystyrene, poly-P-chlorostyrene, polyvinyltoluene and like homopolymers of styrene and substituted styrene, styrene-P-chlorostyrene copolymer, styrene-propylene copolymer, styrene-vinyltoluene copolymer, styrene-vinylnaphthalene copolymer, styrene-methyl acrylate copolymer, styrene-ethyl acrylate copolymer, styrene-butyl acrylate copolymer, styrene-octyl acrylate copolymer, styrene-methyl methacrylate copolymer, styrene-ethyl methacrylate copolymer, styrene-butyl methacrylate copolymer, styrene-methylchloromethacrylate copolymer, styrene-acrylo-nitrile copolymer, styrene-vinyl methyl ether copolymer, styrene-vinyl ethyl ether copolymer, styrene-vinyl methyl ketone copolymer, styrene-butadiene copolymer, styrene-isoprene copolymer, styrene-acrylonitrile-indene copolymer and like styrene copolymers, polyvinyl chloride, polyvinyl acetate, polyethylene, polypropylene, silicone resin, polyester, polyurethane, polyamide, epoxy resin, polyvinyl butyral, resin, modified rosin, terpene resin, phenolic resin xylene resin, aliphatic or alicyclic hydrocarbon resins, aromatic petroleum resins, chlorinated paraffin, paraffin wax, etc. These resins may be used singly or in admixture.

Although various known dyes and pigments are usable as coloring agents, according to the present invention, especially useful for color copy toners are Benzidine Yellow, quinacridone, copper phthalocyanine, etc.

When toners of the present invention were tested in comparison with a known toner containing a commercial Cr complex of 3,5-ditertiary butylsalicylic acid, disclosed in the above-mentioned Japanese Patent Application No. 127726/1978 (and correspondingly U.S. Pat. No. 4,206,064), the toners of the present invention were advantageously found to have outstanding durability due to improved compatibility of the complexes of the present invention with the resin component, and which was not the case with such known toner.

Stated more specifically, the corresponding conventional toner and toners of the present invention were tested for durability by placing each specimen into a 2-liter ball mill pot, driving the pot at a speed of about 50 r.p.m. and determining the amount of triboelectric charges on the specimen and the V-D characteristics thereof with the lapse of time. Consequently, all the specimens of the present invention were found to be much more stable in the amount of triboelectric charges and V-D characteristics than the conventional specimen as well as highly resistant to mechanical agitation. This reveals or confirms that the toners of the present invention are very durable and serviceable for a prolonged period of time.

According to the present invention, therefore, toners having high durability can be prepared with the use of various resins together with the instant metal-containing complex compound. Additionally, the instant metal complex, which serves as an essential component of the toners of the present invention, has an outstanding advantage in that it is colorless or substantially colorless, and therefore may be used efficiently as a charge control agent with the coloring agent also present.

For the preparation of toners, the metal complexes of the present invention are used usually in an amount of substantially between about 0.1 to 10 parts by weight, preferably substantially between about 0.5 to 5 parts by weight, per 100 parts by weight of resin.

The resultant toner of the present invention is advantageously admixed with a carrier in the usual way to provide a developer. Any of the known carriers is usable for this purpose. Examples of useful carriers in this regard are magnetic particles, such as iron particles, glass beads, and such particles or beads coated with a resin.

The present invention will be described with reference to the following examples set forth by way of illustration and not limitation and in which the parts are all by weight unless otherwise specifically indicated:

EXAMPLE 1

Preparation of Cr complex of 2-hydroxy-3-naphthoic acid (Symmetrical)

A 75.2 g quantity of 2-hydroxy-3-naphthoic acid was dispersed in 1500 g of water and 98 g of 40% aqueous solution of $Cr_2(SO_4)_3$ was added to the dispersion. The mixture was heated to 95° to 98° C. A solution of 24 g of caustic soda in 200 g of water was added to the mixture over a period of 1 hour. The mixture was thereafter stirred for 3 hours at 95° to 98° C. The resulting reaction mixture was a slightly yellowish green slurry having a pH of about 3.2. The slurry was filtered, and the filter cake was washed with water until the pH reached 6 to 7 and then dried to give 90 g of Cr complex compound of 2-hydroxy-3-naphthoic acid (hereinafter referred to as "Complex Compound 1").

Subsequently a toner was prepared in the following manner with use of Complex Compound 1.

| | |
|---|---|
| Styrene-butyl methacrylate copolymer ("HIMER SBM 73", product of Sanyo Kasei Co., Ltd.) (Resin component) | 100 parts |
| Carbon black ("Regal 300R", product of Cabot Corp.) (Coloring Agent component) | 5 parts |
| Complex Compound 1 (Charge Control Agent component) | 1 part |

These ingredients were uniformly premixed by a ball mill, then kneaded with hot rolls, cooled, thereafter coarsely ground by a continuous vibrating mill and further pulverized by a jet mill. The particles were classified to obtain a fraction comprising a powdery toner 3 to 15 microns in mean particle size. Five parts of the toner and 95 parts of iron carrier particles were mixed together to prepare a developer. The toner was found to be triboelectrically chargeable to an initial value of $-11.3$ $\mu c/g$. Even after making 50,000 electrostatic copies continuously in the usual manner, the developer was still usable without entailing any reduction in the quality of the copies.

EXAMPLE 2

Preparation of Cr complex of 1-hydroxy-2-naphthoic acid (Symmetrical)

A 75.2 g quantity of 1-hydroxy-2-naphthoic acid was dissolved in 300 g of ethyl cellosolve, and chromium acetate (0.2 equivalent calculated as atomic weight of Cr) and 30 g of urea were added to the solution. The mixture was stirred at 110° to 115° C. for 2 hours. The reaction mixture was in the form of a dark green supernatant liquid. The mixture was cooled to 30° C. and placed into 1 liter of water containing 60 g of 35% hydrochloric acid, whereby a pale yellowish green precipitate was formed. The precipitate was filtered off and washed with water until the pH thereof became 6 to 7. The precipitate was dried to give 85 g of Cr complex compound of 1-hydroxy-2-naphthoic acid (hereinafter referred to as "Complex Compound 2").

A toner was prepared in the same manner as in Example 1 except that Complex Compound 2 was used in place of Complex Compound 1. The toner was similarly tested for the amount of initial triboelectric charges and the quality of electrostatic copies. Table 1 set forth hereinbelow shows the results obtained.

EXAMPLE 3

Preparation of Cr complex of 2-hydroxy-3-naphthoic acid and tertiary butylsalicyclic acid (Asymmetrical)

A 53.2 g quantity of $CrCl_3.6H_2O$ was dissolved in 600 g of water, 38.8 g of tertiary butylsalicylic acid was added to the solution, and the mixture was stirred with heating at 95° to 98° C. Subsequently, 63 g of diethanolamine diluted with 200 g of water was added dropwise to the mixture over a period of 60 minutes. When the resulting reaction mixture was spotted on filter paper, a gray liquid oozed out around a separated cake. Fifteen minutes later, 37.6 g of 2-hydroxy-3-naphthoic acid was added to the mixture, and the resulting mixture was further reacted at 95° to 98° C. When the mixture was checked in about 30 minutes by spotting in the same manner as above, a colorless liquid oozed out. The mixture was stirred for two hours. The reaction mixture had a pH of about 3 and was in the form of a slightly yellowish green slurry. The slurry was filtered, and the filter cake was washed with water and dried to provide 80 g of a Cr complex compound (hereinafter referred to as "Complex Compound 3").

A toner was prepared in the same manner as in Example 1 with the exception of using Complex Compound 3 instead of Complex Compound 1 and was similarly tested for the amount of initial triboelectric charges and the quality of electrostatic copies. Table I set forth hereinbelow shows the results obtained.

EXAMPLE 4

| | |
|---|---|
| Styrene resin ("Piccolastic D-125", product of Esso Petrochemical Co.) | 100 parts |
| Carbon black ("Regal 300R", product of Cabot Corp.) | 5 parts |

-continued

| Complex Compound 1 | 1 part |

A toner was prepared from the above ingredients in the same manner as in Example 1. The amount of triboelectric charges on the toner was $-9.5\ \mu c/g$. Even after making 50,000 electrostatic copies, the developer incorporating the toner was usable without entailing any reduction in the quality of the copies.

EXAMPLE 5

| Epoxy resin ("Epon 1004", product of Shell Chemical Co.) | 100 parts |
| Copper phthalocyanine | 4 parts |
| Complex Compound 2 | 2 parts |

A blue toner was prepared from the above ingredients in the same manner as in Example 1. The amount of triboelectric charges on the toner was $-10.6\ \mu c/g$. Even after making 50,000 electrostatic copies, the developer incorporating the toner was usable without entailing any reduction in the quality of the copies.

EXAMPLE 6

Preparation of Co complex of 2-hydroxy-3-naphthoic acid (Symmetrical)

A 75.2 g quantity of 2-hydroxy-3-naphthoic acid was dispersed in 1000 g of water, and 100 g of cobalt acetate (tetrahydrate) and 80 g of sodium acetate (trihydrate) were added to the dispersion. The mixture was heated to 95° to 98° C. and maintained at this temperature for 3 hours with stirring. When the mixture was maintained at a pH of about 8 in the meantime, a pale blue precipitate was formed. The mixture was cooled to 60° C., and the pH thereof was adjusted to 4 with a dilute mineral acid, as in Example 2, whereby the precipitate changed to a very slightly rose-color precipitate. The precipitate was filtered off, washed with water until the pH adjusted to 6 to 7 and dried, giving 80 g of Co complex compound of 2-hydroxy-3-naphthoic acid (hereinafter referred to as "Complex Compound 4").

A toner was prepared in the same manner as in Example 1 with the exception of using Complex Compound 4 instead of Complex Compound 1 and was similarly tested for the quality of copies and initial triboelectric charges. Table 1 set forth hereinbelow shows the results obtained.

EXAMPLE 7

Preparation of Fe complex of 2-hydroxy-3-naphthoic acid (Symmetrical)

The procedure of Example 1 was repeated with the exception of using 54 g of ferric chloride (hexahydrate) in place of the chromium compound to obtain 80 g of a brown complex compound (hereinafter referred to as "Complex Compound 5").

A toner was prepared in the same manner as in Example 4 with the exception of using Complex Compound 5 instead of Complex Compound 1 and was similarly tested for the quality of copies and initial triboelectric charges. Table 1 set forth hereinbelow shows the results obtained.

EXAMPLE 8

Preparation of Cr complex of n-butyl-2-hydroxy-3-naphthoic acid (Symmetrical)

The procedure of Example 2 was repeated with the exception of using 97.6 g of n-butyl-2-hydroxy-3-naphthoic acid instead of 1-hydroxy-2-naphthoic acid to obtain 105 g of the desired complex compound (hereinafter referred to as "Complex Compound 6").

A toner was prepared in the same manner as in Example 5 with the exception of using Complex Compound 6 in place of Complex Compound 2 and was similarly tested for the quality of copies and initial triboelectric charges. Table 1 set forth hereinbelow shows the results obtained.

EXAMPLE 9

Preparation of Cr complex of 5,6,7,8-tetrahydro-2-hydroxy-3-naphthoic acid (Symmetrical)

The procedure of Example 2 was repeated with the exception of using 76.8 g of 5,6,7,8-tetrahydro-2-hydroxy-3-naphthoic acid in place of 1-hydroxy-2-naphthoic acid to obtain 85 g of a light green complex compound (hereinafter referred to as "Complex Compound 7").

A toner was prepared in the same manner as in Example 5 with the exception of using Complex Compound 7 in place of Complex Compound 2 and was similarly tested for the quality of copies and initial triboelectric charges. Table 1 set forth hereinbelow shows the results obtained.

REFERENCE EXAMPLE 1

(Comparison)

A toner was prepared with use of a known metal-containing complex dye "VALIFAST Black #3804 (product of Orient Kagaku Kogyo K.K., C.I. Acid Black 63) in place of Complex Compound 1 used above. A developer was prepared from the toner and tested in the same manner as above. Although electrostatic copies of the same quality as in the foregoing examples according to the present invention were obtained initially, the developer produced undesirable changes resulting in a reduction in the quality after making about 50,000 copies. Thus, the later obtained copies were inferior to those obtained in the foregoing examples according to the present invention.

REFERENCE EXAMPLE 2

(Comparison)

A toner was prepared in the same manner as in Example 1 except that Complex Compound 1 was omitted therefrom. A developer was prepared with the use of this toner and tested similarly. The test revealed that even in the initial stage of the electrostatic copying operation, the developer (i.e. in the absence of the complex compound according to the present invention) produced markedly fogged toner images and had no ability to reproduce thin lines.

Table 1 below shows the initial triboelectric charges on the toners obtained in each of the above examples and reference examples (comparisons) and the quality of the electrostatic copies obtained with use of the toners. The results are evaluated according to the following criteria:

O: Good
Δ: Fair
X: Poor

TABLE 1

|  | Initial triboelectric charge (μc/g) | Toner filming | Fog | Image density | Fixing properties | Thin line reproducibility | Overall copy quality* |
|---|---|---|---|---|---|---|---|
| Example 1 | −11.3 | 0 | 0 | 0 | 0 | 0 | 0 |
| Example 2 | −9.2 | 0 | 0 | 0 | 0 | 0 | 0 |
| Example 3 | −10.7 | 0 | 0 | 0 | 0 | 0 | 0 |
| Example 4 | −9.5 | 0 | 0 | 0 | 0 | 0 | 0 |
| Example 5 | −10.6 | 0 | 0 | 0 | 0 | 0 | 0 |
| Example 6 | −9.4 | 0 | 0 | 0 | 0 | 0 | 0 |
| Example 7 | −11.2 | 0 | 0 | 0 | 0 | 0 | 0 |
| Example 8 | −9.8 | 0 | 0 | 0 | 0 | 0 | 0 |
| Example 9 | −10.8 | 0 | 0 | 0 | 0 | 0 | 0 |
| Ref. Ex. 1 | −11.0 | 0 | 0 | 0 | 0 | Δ | Δ |
| Ref. Ex. 2 | 0.50 | X | X | X | X | X | X |

*After making 50,000 copies continuously

Thus, advantageously, the present invention provides a novel charge control agent for a toner for developing electrostatic images comprising a metal complex having the formula (I) above.

More specifically, in said formula (I), a or b, only one of which is present, is a corresponding fused benzene or cyclohexene ring moiety, i.e. a counterpart moiety to the adjacent benzene ring shown, which is optionally substituted with at least one alkyl substituent having 4 to 9 carbon atoms, e.g. mono, di or tri-substituted by such alkyl substituent or substituents, including both straight and branched chain substituents such as butyl, pentyl, hexyl, heptyl, octyl and nonyl, and $R_1$ and $R_2$ are hydrogen or alkyl substituents, i.e. oleophilic substituents, having 4 to 9 carbon atoms, including both straight and branched chain substituents such as butyl to nonyl as enumerated immediately hereinabove, or $R_1$ and $R_2$ together form a corresponding said fused benzene or cyclohexene ring moiety, i.e., a like counterpart moiety to the adjacent benzene ring shown, which similarly is optionally substituted with at least one alkyl substituent having 4 to 9 carbon atoms, e.g. mono, di or tri-substituted by such alkyl substituent or substituents, including both straight and branched chain substituents such as butyl to nonyl as enumerated hereinabove, provided that both $R_1$ and $R_2$ are not hydrogen at the same time.

In this regard, Me is either chromium, cobalt or iron, i.e. in trivalent chromic, cobaltic and ferric corresponding metal form, whereas X may be any appropriate cation such as hydrogen or alkali metal such as sodium.

As will be appreciated from the foregoing, the metal complex may be desirably provided as a symmetrical or asymmetrical complex.

According to one feature of the invention, in said formula (I), a or b, only one of which is present, is a corresponding fused benzene ring moiety, and $R_1$ and $R_2$ together form a corresponding fused benzene ring moiety, and preferably these moieties are the same and the metal complex is a symmetrical metal complex.

According to another feature of the invention, in said formula (I), a or b, about only one of which is present, is a corresponding fused benzene ring moiety, $R_1$ is hydrogen and $R_2$ is alkyl having 4 to 9 carbon atoms, e.g. a butyl such as tertiary butyl.

According to a further feature of the invention, in said formula (I), a or b, only one of which is present, is a corresponding fused benzene ring moiety which is substituted with at least one alkyl substituent having 4 to 9 carbon atoms, e.g. mono substituted with a butyl such as normal butyl, and $R_1$ and $R_2$ together form a corresponding fused benzene ring moiety which is preferably similarly substituted with at least one alkyl substituent having 4 to 9 carbon atoms, e.g. mono substituted with a butyl of the aforesaid type, and more preferably these moieties are the same and the metal complex is a symmetrical metal complex.

According to a still further feature of the present invention, in said formula (I), a or b, only one of which is present, is a corresponding fused cyclohexene, i.e., tetrahydro saturated, ring moiety, and $R_1$ and $R_2$ together form a corresponding said fused cyclohexene ring moiety, and preferably these moieties are the same and the metal complex is a symmetrical metal complex.

Advantageously, the instant metal complex charge control agent may be provided in the form of a suitable toner composition containing a toner resin component and a coloring agent component together therewith, e.g. in finely divided and intimately intermixed form, preferably with the instant metal complex charge control agent being present in the toner composition in a charge control effective amount of substantially between about 0.1 to 10 parts by weight per 100 parts of the toner resin. In turn, the toner composition is desirably admixed with a finely divided carrier therefor to provide a developer for developing electrostatic images.

More broadly, however, the present invention contemplates an appropriate toner composition containing the instant metal complex charge control agent along with a toner resin suitable for developing electrostatic images in admixture therewith. The instant metal complex is efficiently present in the composition in a charge control effective amount for controlling the charge of the toner resin, and more especially a coloring agent is also present in such composition.

Stated another way, the present invention comtemplates a metal complex having the formula

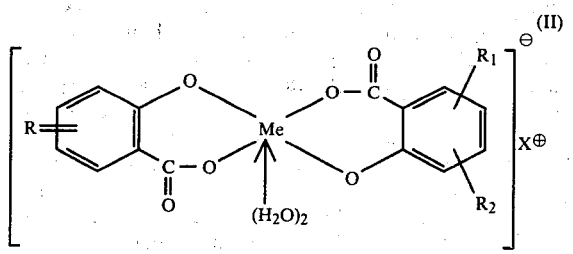

(II)

wherein R is selected from the group consisting of a corresponding unsubstituted or $C_4$ to $C_9$ alkyl substituted, e.g. mono, di or tri-substituted by such alkyl substituent or substituents, including both straight and branched chain substituents such as butyl to nonyl as enumerated hereinabove, fused benzene or cyclohexene ring moiety, i.e, a counterpart moiety to the adjacent benzene ring shown, and which is in a position vicinally ortho or meta to the oxygen linkage —O— to Me and remote from the carbonyloxy linkage

to Me, and $R_1$ and $R_2$ are selected from the group consisting of hydrogen or $C_4$ to $C_9$ alkyl, including both straight and branched substituents, i.e., oleophilic substituents, such as butyl to nonyl as enumerated hereinabove, or $R_1$ and $R_2$ together form a corresponding unsubstituted or similarly $C_4$ to $C_9$ alkyl substituted, e.g. mono, di or tri-substituted by such alkyl substituent or substituents, including both straight and branched substituents such as butyl to nonyl as enumerated hereinabove, fused benzene or cyclohexene ring moiety, i.e, a like counterpart moiety to the adjacent benzene ring shown, provided that both $R_1$ and $R_2$ are not hydrogen at the same time, with Me being a metal selected from the group consisting of chromium, cobalt and iron, and X being a corresponding counter ion, preferably selected from the group consisting of hydrogen and alkali metal such as sodium.

Such metal complex advantageously is substantially colorless as well as capable of negatively charging toner resins for developing electrostatic images, and essentially constitutes the substantially equimolar reaction product, with a corresponding reactive compound containing the metal Me, of substantially one molar equivalent of a first member selected from the group consisting of a corresponding hydroxy-naphthoic acid and a corresponding tetrahydro-hydroxy-naphthoic acid, and substantially one molar equivalent of a second member selected from the group consisting of a corresponding salicylic acid, a corresponding hydroxy-naphthoic acid and a corresponding tetrahydro-hydroxy-naphthoic acid.

Such metal complex may be provided as a symmetrical or asymmetrical metal complex depending upon the selection of the aforesaid first member and second member reactants.

More particularly, in formula (II) above, R may be a corresponding unsubstituted fused benzene ring moiety, and $R_1$ and $R_2$ may together form a corresponding fused benzene ring moiety, or alternatively, $R_1$ may be hydrogen and $R_2$ may be $C_4$ to $C_9$ alkyl such as butyl, and especially tertiary butyl. Also, R may be a corresponding $C_4$ to $C_9$ alkyl substituted, such as mono substituted, e.g. butyl, and especially normal butyl, fused benzene ring moiety, and $R_1$ and $R_2$ may together form a corresponding $C_4$ to $C_9$ alkyl substituted, such as mono substituted, e.g. butyl, and especially normal butyl, fused benzene ring moiety. Besides, R may be a corresponding unsubstituted fused cyclohexene, i.e. tetrahydro saturated, ring moiety, and $R_1$ and $R_2$ together may form a corresponding said unsubstituted fused cyclohexene ring moiety.

In all instances, the metal-containing complex or complex compound or charge control agent, according to the present invention, possesses good compatibility and wettability with the toner resin component, is capable of negatively charging the corresponding toner without impairing the charging properties of the contemplated coloring agent component such as a metal-containing dye, and is thereby useful as a charge control agent for attaining toners having high durability and comprising chargeable particles of uniform quality. In particular, the instant metal-containing complex or complex compound or charge control agent is distinguished by its substantially colorless property and its contemplation of both a highly aromatic compound moiety and a highly oleophilic compound moiety preferably containing at least one alkyl substituent.

While various specific embodiments of the invention have been shown and described in detail to illustrate the application of the principles and inherent features of the invention, it will be understood that the invention may be embodied otherwise without departing from such principles and inherent features.

What is claimed is:

1. A toner composition for developing electrostatic images in the form of an admixture of a toner resin and a charge control agent comprising a metal complex having the formula

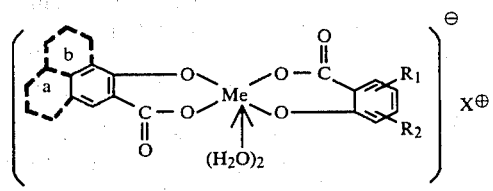

wherein a or b, only one of which is present, is a corresponding fused benzene or cyclohexene ring moiety which is optionally substituted with a least one alkyl substituent having 4 to 9 carbon atoms, $R_1$ and $R_2$ are hydrogen or alkyl substituents having 4 to 9 carbon atoms or together form a corresponding fused benzene or cyclohexene ring moiety which is optionally substituted with at least one alkyl substituent having 4 to 9 carbon atoms, provided that both $R_1$ and $R_2$ are not hydrogen at the same time, Me is Cr, Co or Fe, and X is a corresponding counter ion.

2. The composition according to claim 1, wherein the charge control agent is present in a charge control effective amount for controlling the charge of the toner resin.

3. The composition according to claim 2, wherein a coloring agent is also present therein.

4. The composition according to claim 1, wherein the metal complex is a symmetrical metal complex.

5. The composition according to claim 1, wherein the metal complex is an asymmetrical metal complex.

6. The composition according to claim 1, wherein Me is chromium.

7. The composition according to claim 1, wherein Me is cobalt.

8. The composition according to claim 1, wherein Me is iron.

9. The composition according to claim 1, wherein X is selected from the group consisting of hydrogen and alkali metal.

10. The composition according to claim 1, wherein X is hydrogen.

11. The composition according to claim 1, wherein X is sodium.

12. The composition according to claim 1, wherein a or b, only one of which is present, is a corresponding fused benzene ring moiety and $R_1$ and $R_2$ together form a corresponding fused benzene ring moiety.

13. The composition according to claim 12, wherein the metal complex is a symmetrical metal complex.

14. The composition according to claim 1, wherein a or b, only one of which is present, is a corresponding fused benzene ring moiety, $R_1$ is hydrogen and $R_2$ is alkyl having 4 to 9 carbon atoms.

15. The composition according to claim 1, wherein a or b, only one of which is present, is a corresponding fused benzene ring moiety which is substituted with at least one alkyl substituent having 4 to 9 carbon atoms, and $R_1$ and $R_2$ together form a corresponding fused benzene ring moiety which is substituted with at least one alkyl substituent having 4 to 9 carbon atoms.

16. The composition according to claim 15, wherein the metal complex is a symmetrical metal complex.

17. The composition according to claim 1, wherein a or b, only one of which is present, is a corresponding fused cyclohexene ring moiety, and $R_1$ and $R_2$ together form a corresponding fused cyclohexene ring moiety.

18. The composition according to claim 17, wherein the metal complex is a symmetrical metal complex.

19. The composition according to claim 1, wherein a coloring agent is also present therein, and the composition is in finely divided intimately intermixed form.

20. A toner composition for developing electrostatic images in the form of an admixture of a toner resin and a charge control agent comprising a metal complex having the formula

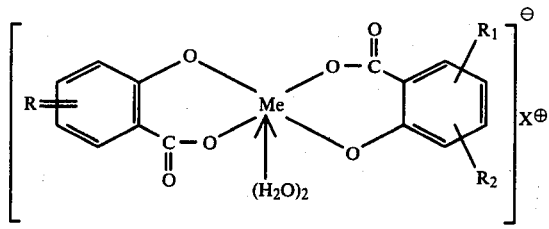

wherein R is selected from the group consisting of a corresponding unsubstituted or $C_4$ to $C_9$ alkyl substituted fused benzene or cyclohexene ring moiety which is in a position vicinally ortho or meta to the oxygen linkage to Me and remote from the carbonyloxy linkage to Me, $R_1$ and $R_2$ are selected from the group consisting of hydrogen or $C_4$ to $C_9$ alkyl or together form a corresponding unsubstituted or $C_4$ to $C_9$ alkyl substituted fused benzene or cyclohexene ring moiety, provided that both $R_1$ and $R_2$ are not hydrogen at the same time, Me is a metal selected from the group consisting of chromium, cobalt and iron, and X is a corresponding counter ion, said metal complex being substantially colorless as well as capable of negatively charging toner resins for developing electrostatic images, and constituting the substantially equimolar reaction product, with a corresponding compound containing the metal Me, of substantially one molar equivalent of a first member selected from the group consisting of a corresponding hydroxy-naphthoic acid and a corresponding tetrahydro-hydroxy-naphthoic acid, and substantially one molar equivalent of a second member selected from the group consisting of a corresponding salicylic acid, a corresponding hydroxynaphthoic acid and a corresponding tetrahydro-hydroxy-naphthoic acid.

21. The composition according to claim 20, wherein a coloring agent is also present therein.

22. The composition according to claim 20, wherein the metal complex is a symmetrical metal complex.

23. The composition according to claim 20, wherein the metal complex is an asymmetrical metal complex.

24. The composition according to claim 20, wherein X is selected from the group consisting of hydrogen and alkali metal.

25. The composition according to claim 20, wherein Me is chromium and X is hydrogen.

26. The composition according to claim 20, wherein R is a corresponding unsubstituted fused benzene ring moiety, and $R_1$ and $R_2$ together form a corresponding fused benzene ring moiety.

27. The composition according to claim 20, wherein R is a corresponding unsubstituted fused benzene ring moiety, $R_1$ is hydrogen and $R_2$ is $C_4$ to $C_9$ alkyl.

28. The composition according to claim 20, wherein R is a a corresponding $C_4$ to $C_9$ alkyl substituted fused benzene ring moiety, and $R_1$ and $R_2$ together form a corresponding $C_4$ to $C_9$ alkyl substituted fused benzene ring moiety.

29. The composition according to claim 20, wherein R is a corresponding unsubstituted fused cyclohexene ring moiety, and $R_1$ and $R_2$ together form a corresponding unsubstituted fused cyclohexene ring moiety.

30. The composition according to claim 19, wherein the charge control agent is present in a charge control effective amount of substantially between about 0.1 to 10 parts by weight per 100 parts of the toner resin.

31. The composition according to claim 19 wherein the toner composition is admixed with a finely divided carrier therefor to provide a developer for developing electrostatic images.

* * * * *

UNITED STATES PATENT OFFICE
CERTIFICATE OF CORRECTION

Patent No. 4,404,271      Dated September 13, 1983

Inventor(s) Kawagishi et al

It is certified that error appears in the above-identified patent and that said Letters Patent are hereby corrected as shown below:

On the title page:

Change the inventors names from

"Yoji Kawagishi, Yukihiko Ishida, Kazuhiro Ishikawa" to

--Yoji Kawagishi, Yukihiko Ishida, Kazuhiro Ishikawa, Masahiro Otsuka --.

Signed and Sealed this

Twenty-first Day of February 1984

[SEAL]

*Attest:*

GERALD J. MOSSINGHOFF

*Attesting Officer*     *Commissioner of Patents and Trademarks*